US005760255A

United States Patent [19]

Vorbrüggen et al.

[11] Patent Number: 5,760,255
[45] Date of Patent: Jun. 2, 1998

[54] PROCESS FOR THE CONVERSION OF HYDROXYL GROUPS INTO THE CORRESPONDING FLUORINE COMPOUNDS

[75] Inventors: Helmut Vorbrüggen; Bärbel Bennua-Skalmowski, both of Berlin, Germany

[73] Assignee: Bayer AG, Leverkusen, Germany

[21] Appl. No.: 666,446

[22] PCT Filed: Oct. 25, 1995

[86] PCT No.: PCT/EP95/04192

§ 371 Date: Jun. 25, 1996

§ 102(e) Date: Jun. 25, 1996

[87] PCT Pub. No.: WO96/13474

PCT Pub. Date: May 9, 1996

[30] Foreign Application Priority Data

Oct. 26, 1994 [DE] Germany ............ 44 39 488.8

[51] Int. Cl.$^6$ .................. C07J 1/00; C07J 9/00; C07J 17/16; C07J 19/08
[52] U.S. Cl. .................. 552/502; 552/540; 570/127; 570/261
[58] Field of Search .................. 552/540, 502; 570/127, 261

[56] References Cited

U.S. PATENT DOCUMENTS 3,914,265  10/1975  Middleton .................. 260/397.3

OTHER PUBLICATIONS

Bennua-skalmowski et al., "The reaction of perfluorobutanesulfonyl fluoride with alcohols in the presence of 4-dialkylaminopyridines." Bull. Soc. Chim. Belg. vol. 103, 453–461, 1994.

Knox et al., Steroids. CCXL. The Reaction of Steroidal Alcohols with 2-Chloro-1,1,2-trifluorotriethylamine, J. Am. Chem. Soc., vol. 29, pp. 2187-2194, Aug. 1964.

John A. Wilkinson, Recent Advances in the Selective Formation of the C–F Bond, Chem. Rev., vol. 92, No. 4, pp. 505-519, 1992.

Bennua-Skalmowski et al., A Facile Conversion of Primary or Secondary Alcohols with n-Perfluorobutane-sulfonyl Fluoride/1,8-Diazabicyclo[5.4.0]undec-7-ene into their Corresponding Fluorides, Tetrahedron Letters, vol. 36, No. 15, pp. 2611-2614, 1995.

Primary Examiner—José G. Dees
Assistant Examiner—Barbara Badio
Attorney, Agent, or Firm—Connolly & Hutz

[57] ABSTRACT

The invention is drawn to a process for the conversion of primary and secondary alcohols into the corresponding fluorine compounds in the presence of an organic solvent, 2–3 equivalents of a strong base and perfluoroalkylsulphonyl fluorides, such as perfluorobutanesulphonyl fluoride or higher homologues.

2 Claims, No Drawings

PROCESS FOR THE CONVERSION OF HYDROXYL GROUPS INTO THE CORRESPONDING FLUORINE COMPOUNDS

This invention relates to novel processes for the conversion of hydroxyl groups into the corresponding fluorine compounds, wherein primary and secondary alcohols are reacted in absolute organic solvents with perfluorobutanesulphonyl fluoride or higher homologues, such as perfluorooctanesulphonyl fluoride, in the presence of 2–3 equivalents of strong organic bases.

The process which is at present most frequently used to introduce fluorine atoms into organic molecules involves reacting primary and secondary aliphatic hydroxyl groups with diethylaminosulphur trifluoride (DAST) in a single reaction stage to yield the corresponding fluorine compounds (M. Hudlicky, Organic Reactions 35, 513; J. A. Wilkinson, Chem. Rev. 92, 505–519 (1992)).

The disadvantage of this process is that the DAST used in the reaction is relatively costly. Moreover, the yields of the corresponding fluorine compounds, for example in the reaction of 3-β-hydroxycholestanol with DAST to yield 3-α-fluorocholestane, are only around 40%.

It has now surprisingly been found that, in sulphonylation reactions with perfluorobutanesulphonyl fluoride, which is produced industrially on a large scale, or the higher homologues thereof, such as perfluorooctanesulphonyl fluoride, primary and secondary alcohols may be reacted smoothly and in sometimes excellent yields to produce the corresponding fluorine compounds in the presence of 2–3 equivalents of strong organic bases, such as for example 1,3-diazabicyclo[5.4.0]undecene (DBU) or 1,3-diazabicyclo[4.3.0]nonene (DBN) together with pentaalkylguanidines, in absolute organic solvents, such as for example toluene.

The present invention accordingly provides processes for the production of fluorine compounds, which processes are characterised in that hydroxyaliphatics of the general formula 1 are reacted with 1–2 equivalents of perfluorobutanesulphonyl fluoride, 2, or higher homologues, such as perfluorooctanesulphonyl fluoride, in the presence of 2–3 equivalents of a strong organic (org.) base, 3, in an inert organic solvent to yield the corresponding fluorine compounds of the general formula 4, in which $R_1$ denotes an optionally substituted linear or branched, aliphatic or araliphatic organic residue and $R_2$ and $R_3$ denote hydrogen, or $R_1$ and $R_2$ designate optionally substituted linear or branched, aliphatic or araliphatic residues and $R_3$ is hydrogen, in accordance with the reaction

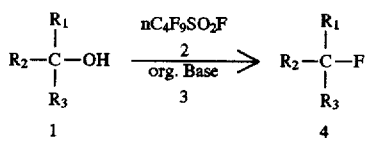

Aliphatic or araliphatic polycyclic ring systems are, for example, 3-hydroxy- or 17-hydroxysteroids or hydroxyprostane esters.

Strong organic bases which may be considered are, in principle, those having a $P_{K_a}$ of $\geq 12$, such as for example all amidine or guanidine bases, such as DBU, DBN, pentamethyl- or pentaisopropylguanidine, which must not contain any reactive NH groups, and novel phosphine/imine bases (Schwesinger bases) such as tert.-butyl-iminotris(dimethylamino)phosphorane and 1'-tert.-butyl-4,4,4-tris(dimethylamino)-2,2-bis-[tris(dimethylamino)phosphoranylideneamino]-2$\lambda^5$,4$\lambda^5$-catenadi(phosphazene).

The reactants are reacted in an inert anhydrous solvent such as toluene, benzene, xylene, anisole, diethyl ether, tetrahydrofuran, 1,4-dioxane, methyl tert.-butyl ether, acetonitrile, sulpholane or ethyl acetate, preferably at $-10° \to +24°$ C., wherein the volatile n-perfluorobutanesulphonyl fluoride, 2, (boiling point 64° C.) is slowly added dropwise with stirring to the solution or suspension of a hydroxy compound, 1, and a strong organic base, 3. The strong dependency of the reaction rate of fluoride formation upon the configuration of the secondary alcohol is surprising. 3-β-Hydroxycholestane with an equatorial hydroxy group reacts very smoothly at an approximately 60% yield to give 3-α-fluorocholestane, while 3-α-hydroxyandrostane with an axial hydroxyl group is much more slowly reacted to 3-β-fluoroandrostane.

The compounds which may be produced using the process are of great interest inter alia for the production of pharmaceuticals and agrochemicals (cf. R. E. Banks, D. W. A. Sharp and I. C. Tatlow, eds., Fluorine: The First Hundred Years, Elsevier Seq., 1986) and of fluoropharmaceuticals (I. T. Welck, S. Esra-Kishman, Fluorine in Bioorganic Chemistry, John Wiley, N.Y., 1991).

The following practical examples illustrate the process according to the invention, but without limiting it.

EXAMPLES

1. Production of 3-fluoropropylbenzene 2.7 ml (15 mmol) of perfluorobutanesulphonyl fluoride were added to a solution of 1.36 g (10 mmol) of 3-phenyl-1-propanol and 4.56 g (30 mmol) of DBU in 80 ml of absolute toluene, whereupon the reaction temperature rose to 37°. According to thin layer chromatography, after 1 hour at 24° all the 3-phenyl-1-propanol had reacted. After shaking with ice-cold NaHCO$_3$ solution, followed by a saturated NaCl solution and a saturated citric acid solution and, finally, again with a saturated NaCl solution, the toluene solution was dried with Na$_2$SO$_4$ and analysed by GC/MS. Analysis revealed, in addition to a little allylbenzene, 86% of 3-fluoropropylbenzene (=1-fluoro-3-phenylpropane).

2. Production of 3-α-fluorocholestane a) 1.13 g (3.75 mmol) of perfluorobutanesulphonyl fluoride were added at +2° C. to a solution of 0.97 g (2.5 mmol) of 3-β-hydroxycholestane and 1.12 ml (7.5 mmol) of DBU in 20 ml of absolute toluene, wherein the temperature rose to 10° C. After 1 hour at +2° C., the mixture was evaporated and the residue chromatographed in hexane through a column of 50 g of silica gel, wherein after 0.23 g (25%) of $\Delta^2(\Delta^3)$cholestene, 0.37 g (37.75%) of pure 3-α-fluorocholestane, melting point 107°–108° C., were eluted first, followed by 0.27 g (27.55%) of 3-α-fluorocholestane, which contains approximately 5% of 3-β-fluorocholestane. Total yield=approx. 61% of 3-α-fluoro-cholestane.

b) In an analogous reaction in 20 ml of absolute acetonitrile instead of 20 ml of toluene, 11.3% of starting material (3-β-hydroxycholestane) were also recovered after 4 h/24° in addition to 37% of $\Delta^2(\Delta^3)$cholestene and 37% of 3-α-fluorocholestane.

c) In an analogous test with 2.0 g (7.5 mmol) of pentaisopropylguanidine instead of DBU in toluene, 0.49 g (50%) of 3-α-fluorocholestane were obtained.

d) In another analogous test with DBN instead of DBU in toluene, approximately 41.8% of 3-α-fluorocholestane were obtained in addition to 41.3% of $\Delta^2(\Delta^3)$cholestene.

e) Identical tests with perfluorooctanesulphonyl fluoride gave the same yields of 3-α-fluorocholestane.

3. Production of 3-β-fluoroandrostane

A solution of 2.38 g (5 mmol) of 3-α-hydroxyandrostane and 1.64 ml (11 mmol) of DBU in 60 ml of absolute toluene was evaporated to 20 ml by heating to 120° (oil bath temperature) and distillation, cooled to 24° and 1.66 g (5.5 mmol) of perfluorobutanesulphonyl fluoride added, wherein the reaction mixture rose slightly in temperature and became yellow. Since starting material was still present after 18 h/24°, a further 0.3 g (2 mmol) of DBU and 0.3 g (1 mmol) of perfluorobutanesulphonyl fluoride were added, whereupon virtually all the 3-α-hydroxyandrostane had reacted after 1 h/24°. After evaporation, the crude reaction product in $CH_2Cl_2$ was evaporated with approximately 5–10 g of silica gel and the silica gel was introduced into a prepared column of 70 g of silica gel slurry-packed with hexane and was eluted with hexane. The first 250 ml of hexane eluted 0.57 g (44.2%) of $\Delta^3(\Delta^3)$androstene, while the following 200 ml of hexane yielded 0.68 g (47.5%) of 3-β-fluoroandrostane, melting point 93°–95° C., and hexane/ether (1:1, 250 ml) yielded approximately 0.070 g (5%) of unreacted 3-α-hydroxyandrostane.

4. Production of 3-methoxy-17-α-fluoro-$\Delta^{1,3,5(10)}$-oestratriene 3.77 g=2.24 ml (12.5 mmol) of perfluorobutanesulphonyl fluoride were added at 24° to 2.86 g (10 mmol) of oestradiol methyl ether, 3.73 ml (25 mmol) of DBU in 80 ml of absolute toluene, wherein the temperature of the reaction mixture rose to 32°. Since some oestradiol methyl ether was still present after 72 h/24°, a further 0.75 ml (5 mmol) of DBU and 0.45 ml (2.5 mmol) of perfluorobutanesulphonyl fluoride were added, whereupon the reaction was complete after 2 h. Chromatography in hexane through a column of 50 g of silica gel, after initial runnings of approximately 500 ml containing four unsaturated oestratrienes, yielded in the next 30 ml of hexane 0.16 g of pure 3-methoxy-17-α-fluoro-$\Delta^{1,3,5(10)}$-oestratriene, melting point 94°–96° (literature, L. H. Knox et al.: *J. Org. Chem.* 29, 2187 (1964))—melting point 96°–98°, on reaction of oestradiol methyl ether with 2-chloro-1,1,2-trifluorotriethylamine - 26% of 17-α-fluorine compound). GC/MS analysis of the mother liquors revealed, in addition to the four possible unsaturated oestratrienes, a total yield of 43% of 3-methoxy-17-α-fluoro-$\Delta^{1,3,5(10)}$-oestratriene.

Reactions of 11a-hydroxysteroids with perfluorobutanesulphonyl fluoride/DBU are described in *Tetrahedron Letters* 36, 2611 (1995).

We claim:

1. Process for the production of fluorine compounds, characterised in that hydroxyaliphatics, aromatics or enol compounds of the general formula 1

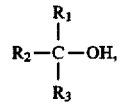

are reacted with 1–2 equivalents of perfluorobutanesulphonyl fluoride, or perfluorooctanesulphonyl fluoride in the presence of 2–3 equivalents of a strong organic base, which must not contain any reactive NH groups, in an inert organic solvent to yield the corresponding fluorine compound of the general formula 4,

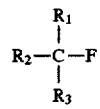

in which $R_1$ denotes an optionally substituted linear or branched, aliphatic or araliphatic hydrocarbon
and
$R_2$ and $R_3$ denote hydrogen,
or
$R_1$ and $R_2$ designate optionally substituted linear or branched, aliphatic or araliphatic hydrocarbons
and
$R_3$ is hydrogen,
or
$R_1$ and $R_2$ form a 4–8 or greater-membered aliphatic ring, which may in turn be part of an aliphatic or araliphatic polycyclic ring system
and
$R_3$ is hydrogen.

2. Process for the production of fluorine compounds according to claim 1, wherein the aliphatic or araliphatic polycyclic ring systems selected from the group consisting of 3-hydroxy or 17-hydroxysteroids and hydroxyprostane esters.

* * * * *

UNITED STATES PATENT AND TRADEMARK OFFICE
CERTIFICATE OF CORRECTION

PATENT NUMBER: 5,760,255

DATED: June 2, 1998

INVENTOR(S): Vorbrüggen et al.

It is certified that there is an error that appears in the above-identified patent and that said Letters Patent is hereby corrected as shown below:

In column 4, line 45 (claim 2) after the word "systems", the word - - are - - should be inserted.

Signed and Sealed this

Tenth Day of April, 2001

Attest:

NICHOLAS P. GODICI

Attesting Officer     Acting Director of the United States Patent and Trademark Office